United States Patent [19]

Cavitt

[11] 4,102,820

[45] Jul. 25, 1978

[54] SILVER CATALYST FOR ETHYLENE EPOXIDATION

[75] Inventor: Stanley B. Cavitt, Austin, Tex.

[73] Assignee: Texaco Development Corp., New York, N.Y.

[21] Appl. No.: 644,704

[22] Filed: Dec. 29, 1975

[51] Int. Cl.$^2$ .................... B01J 21/04; B01J 23/66
[52] U.S. Cl. ............................ 252/463; 252/476; 260/348.34
[58] Field of Search ................ 252/463, 476; 260/348.5 R

[56] References Cited

U.S. PATENT DOCUMENTS 3,702,259    11/1972    Nielsen ........................ 252/463 X

*Primary Examiner*—W. J. Shine
*Attorney, Agent, or Firm*—Carl G. Ries; Thomas H. Whaley; Walter D. Hunter

[57] ABSTRACT

A novel, stable, activated silver catalyst useful in the vapor phase epoxidation of ethylene with an oxygen-containing epoxidizing agent is provided. The novel catalyst is prepared by impregnating certain inorganic porous supports with a silver caboxylate/amine complex impregnating solution of a silver carboxylate solubilized in an amine-containing complexing agent selected from:

(a) diamines wherein at least one amino moiety is primary or secondary, but no more than one is primary;

(b) polyamines containing at least three amino moieties wherein at least one is primary or secondary; or (c) amino ethers containing at least one ether linkage and at least one amino moiety which is primary or secondary;

and heating the impregnated support at temperatures of from about 50° C to about 300° C to evaporate volatiles, decompose the complex and activate the catalyst. The novel catalyst shows excellent mechanical strength and superior yield and selectivity in air epoxidation processes.

22 Claims, No Drawings

SILVER CATALYST FOR ETHYLENE EPOXIDATION

BACKGROUND OF THE INVENTION

1. Field of the Invention

This invention relates to supported silver epoxidation catalysts and more particularly to a method of preparing a stable, activated silver epoxidation catalyst from specific silver carboxylate/amine complexes.

2. Description of the Prior Art

Supported silver catalysts have long been used for the air oxidation of ethylene and more recently in a so-called "oxygen process." Although the first reference to the use of silver as such a catalyst was made by Walter in British Pat. No. 21,941 (1905), it was not until some thirty years later that the first disclosures were made of the use of silver as a catalyst in the vapor phase oxidation of ethylene to ethylene oxide. See Société Francaise De Catalyse Généralisée, French Pat. No. 729,952 (1932); and Lefort, U.S. Pat. No. 1,998,878 (1935).

Since silver is expensive, optimizing the amount of silver employed in a supported catalyst for a desired conversion and selectivity to products has been widely investigated. A variety of techniques have been developed for the depositing of relatively small, but highly active amounts of silver on surfaces of non-silver supports such as alumina. For example, McKim and Cambron in *Canadian Journal of Research*, Volume 27, Section B (1949) at 813–827, describe a method for depositing particulate silver on a support by decomposing silver oxalate in aqueous ethanolamine at 60° C and forming a paste which is applied to the surface of the support. In U.S. Pat. No. 3,043,854 issued July 10, 1962, to Endler, a silver coating formed by decomposition of a silver carbonate slurry is applied to a catalyst support surface.

Recently it has been disclosed that supported silver catalysts can be prepared by impregnating a porous substrate with certain silver containing solutions and evaporating or decomposing the solutions to deposit silver on the substrate. U.S. Pat. No. 3,702,259 to Nielsen describes the use of an aqueous silver oxalate impregnating solution which employs a solubilizing/reducing agent of ethylenediamine, a mixture of ethylenediamine or ethanolamine and ammonia or a mixture of ethylenediamine and ethanolamine. Van Bylandtlaan, in Belgium Pat. 808,278 (1974) employs an aqueous solution of hexamethylenetetramine with an ethylenediamine silver complex to deposit silver on an alumina support by decomposition. Additionally, it has been disclosed in Japanese Pat. No. 71/19,606 to Fujii et al that impregnation of inorganic supports with aqueous silver nitrate/alkanolamine complexes with subsequent thermal decomposition gives supported silver catalysts for ethylene epoxidation.

It has now been discovered that extremely stable, physically durable, supported silver catalysts can be simply produced by impregnating a porous, inorganic substrate with a complex formed by dissolving a silver carboxylate in certain amines and thermally decomposing the complex to deposit the silver on the substrate and activate the silver. Surprisingly, the supported catalysts of the instant invention show high productivity and are more active at a given reactor temperature than the prior art catalysts. Additionally, the instant inventive catalysts show high attrition resistance and surprisingly high mechanical strength. It has further been found that the instant catalysts provide good selectivity in air oxidation processes. This is particularly important in that such processes are not closed systems and some proportion of the unreacted ethylene is lost by venting excess gas.

SUMMARY OF THE INVENTION

According to the broad aspect of the instant invention, a porous, inorganic substrate is impregnated with a silver carboxylate/amine complex impregnating solution and heated at temperatures of from 50° C to 300° C to evaporate volatiles, decompose the complex, and activate the catalyst.

The impregnating solution is formed by dissolving a silver carboxylate in a solubilizing amount of an amine containing complexing agent selected from:

(a) diamines wherein at least one amino moiety is primary or secondary, but no more than one is primary;

(b) polyamines containing at least three amino moieties wherein at least one is primary or secondary; or (c) amino ethers containing at least one ether linkage and at least one amino moiety which is primary or secondary.

DESCRIPTION OF THE PREFERRED EMBODIMENTS

In accordance with a preferred embodiment, the novel supported silver catalyst of the instant invention is prepared in four steps. In a first step, a silver carboxylate/amine complex, as more fully described hereinafter, is prepared by dissolving a silver carboxylate in an excess of a polyalkylene polyamine having terminal primary nitrogen moieties at temperatures sufficient to dissolve the silver carboxylate.

In a second step, an inorganic porous support, as more fully described hereinafter, and preferably a high-purity α-alumina support, is impregnated by immersing the support in the silver carboxylate/amine complex at about atmospheric pressure and then subjecting the immersed support to vacuum at temperatures of from about 20° C to about 40° C. After the vacuum is broken, the excess complex is drained. In a third step, the drained support is heated to evaporate volatiles at temperatures of from about 50° C to 150° C in a forced-air heater for a time from about 1 to about 12 hours. In a final step, the dried, impregnated support is heated in the presence of forced air at temperatures of from about 200° C to about 300° C to decompose the silver carboxylate/amine complex and activate the supported silver catalyst material.

THE IMPREGNATING SOLUTION

The impregnating solution of the instant invention comprises a silver carboxylate/amine complex. The impregnating solution can best be characterized as a homogeneous liquid at impregnating temperatures which is formed by solubilizing a silver salt of an organic acid in a solubilizing amount of certain amine-containing complexing agents. Surprisingly, these silver carboxylate/amine complexes are stable in high solution concentrations at impregnating temperatures, and contain large amounts of silver which are carried to the support, while simultaneously yielding a solution of a viscosity which is suitable for impregnation of porous, inorganic supports.

The silver carboxylate/amine complex impregnating solutions of the instant invention can best be described in terms of their method of preparation. Specifically, a silver salt of an organic acid is dissolved in a solubilizing amount of certain amine-containing complexing agents at temperatures in the range of from about 0° to about 50° C.

The useful silver salts of organic acids can be generally described as silver carboxylates which readily thermally decompose. Such compounds can be carboxylates of mono-carboxylic or poly-carboxylic acids. Preferably, the silver salt is of a monocarboxylic or di-carboxylic acid, wherein the organic moiety contains less than about 10 carbon atoms. Those carboxylates of less than about 10 carbon atoms are preferred in order to obtain a favorable concentration of silver in the organic acid salt, and ultimately thus in the complex solution, while providing for facile thermal decomposition. It should be noted that while silver salts of organic acids containing more than about 10 carbon atoms are useful, they produce a silver amine which becomes increasingly difficult to decompose as the molecular weight increases.

Examples of suitable silver carboxylates include silver carbonate, silver acetate, silver malonate, silver glycolate, silver oxalate, silver formate, silver citrate, silver lactate, silver pyruvate, and the like. The most preferred silver carboxylates are silver oxalate and silver acetate because of availability.

The useful amine containing complexing agents of the instant invention can be generically described as:

(a) diamines wherein at least one amino moiety is primary or secondary provided no more than one amino moiety is primary;

(b) polyamines containing at least three amino moieties wherein at least one is primary or secondary; and, (c) amino ethers containing at least one ether (oxy) linkage wherein at least one amino moiety is primary or secondary.

Although all aliphatic diamines meeting the above criteria are useful as complexing agents, a preferred group of diamines are those compounds of the formula

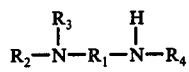

wherein $R_1$ is a straight or branched chain alkylene radical of from 2 to 8 carbon atoms; wherein $R_2$ and $R_3$ are $R_4$ are, independently, hydrogen or an alkyl radical of from 1 to 5 carbon atoms, provided that $R_4$ be hydrogen only when $R_2$ or $R_3$ is alkyl. Exemplary of such compounds are N-methyl-ethylenediamine, N-ethylethylenediamine, N,N'-dimethyl-ethylenediamine, N,N'-diethyl propylenediamine, N-ethyl-N'-methyl ethylenediamine and the like. Another class of useful diamines is piperazine, the N-alkyl substituted piperazines and the C-alkyl substituted piperazines. It should be noted that the symmetrical, lower alkylene primary diamines are not useful or desired complexing agents in accordance with the invention. These compounds alone do not readily form suitable complex solutions with silver salts of carboxylic acids.

While all aliphatic polyamines containing at least three amino moieties wherein at least one is primary are useful as complexing agents, a preferred group is the polyalkylene polyamines of the formula

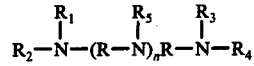

wherein R is a straight or branched chain alkylene radical having from 2 to about 4 carbon atoms, $R_1$, $R_2$, $R_3$, $R_4$ and $R_5$ are, independently, hydrogen or an alkyl radical of from 1 to 5 carbon atoms provided at least one of $R_1$, $R_2$, $R_3$, $R_4$ or $R_5$ is hydrogen; or $R_1$ and $R_2$ or $R_3$ and $R_4$ with the nitrogen to which they are attached form a piperazine ring and n is an integer of from 1 to about 4. Examples include N(aminoethyl)-piperazine, N,N'-bis(2-aminoethyl)piperazine, diethylenetriamine, N-methyldiethylenetriamine, triethylenetetramine and the like. The most preferred polyalkylene polyamine compounds are diethylenetriamine and triethylenetetramine.

The amino ethers that are useful within the scope of the instant invention are the saturated and unsaturated, substituted and unsubstituted aliphatic amino ethers. These compounds may be straight or branched chain, acyclic, alicyclic, heterocyclic, or cyclic. Examples of such compounds include morpholine, the C-substituted morpholines, etc.; the bis(amino alkyl) ethers, the N-alkyl bis(amino alkyl) ethers, etc.; the polyoxyalkylene amines; the polyoxyalkylene polyamines, etc.; the alkoxy alkyl amines; furfuran amines; and the like.

One preferred class of aminoethers is morpholine and the C-alkyl substituted morpholines. Another preferred class is the polyoxyalkyleneamines of molecular weight less than 1,000 and more preferably less than 500. Examples include the polyoxypropylenediamines of molecular weight less than about 400, and a polyoxypropylenetriamine of molecular weight about 400. Both of the above types of compounds contain terminal primary amino groups.

The amount of a particular amine containing complexing agent utilized in forming the silver carboxylate/amine complex impregnating solution is somewhat empirical. Generally that amount of amine complexing agent sufficient to completely dissolve the silver salts, i.e., a solubilizing amount, is utilized. This amount can be readily determined by the skilled artisan in that it is generally that amount sufficient to completely dissolve the silver salt, which can be determined by observation.

As hereinbefore mentioned, it is desirable to have the complex as "rich" as possible in silver. Generally the impregnating solution should contain an amount of about twice that desired in the finished catalyst on a wt. % basis. It is preferable, therefore, to obtain a complex which contains more than about 10 weight % silver in the impregnating solution and more preferably from about 12 to about 25 weight % silver. Normally, a solubilizing amount will be a slight molar excess of the amine containing agent.

When the preferred polyalkylene polyamines are utilized, it is desirable to have from about 1 to about 6 amine equivalents of the polyalkylene polyamine for each equivalent of silver in order to form the optimum complex containing solution.

The silver salt is preferably solubilized in the amine containing agent at temperatures in the range of about 20° C to about 40° C. Temperatures in excess of 50° C are not preferred, since higher elevated temperatures tend to cause accelerated decomposition of the complex.

If desired, solubilizers can be added in order to facilitate dissolution of the silver salt in the amine complexing agent. Examples of such solubilizers include water, aqueous ammonia, and the like. In accordance with a preferred embodiment, water is utilized as the solubilizing agent. Water not only reduces the viscosity of the impregnating solution, reduces the amine required to solubilize the silver salt, and reduces the hazard of handling the solution, but also acts as a solvent for the silver salt/amine complex thus preventing precipitation.

Examples of suitable solubilizers include aqueous methyl amine, ethylamine, diethylamine, triethylamine, and pyridine. It is, however, recognized that the marginal advantages of such solubilizers may be outweighed by the fact that certain lower molecular weight amines or ammonia can form explosive solids. In addition, although not necessary, small amounts of hydrogen peroxide or other suitable oxidizing agents may be added to minimize premature reduction of the silver in the complex.

THE SUPPORT

The support utilized to form the novel silver catalyst of the instant invention can be generally described as a porous, inorganic substrate having those characteristics which are well known in the art and particularly known in the ethylene epoxidation art. Suitable supports which can be used in accordance with the instant invention are glass, alumina, silica, silicaalumina, inert metals, silicon carbide and zirconia. It is essential that the support chosen have a high porosity, low surface area and a controlled pore size. Preferably, from about 70% to 100% of the pore diameters are between 1 and 30$\mu$ and more preferably between 1 and about 10$\mu$.

A preferred support media has an average pore diameter of from about 4 to about 6$\mu$ with a pore volume of from about 0.3 to about 0.6 cc/g and has a surface area less than about 1 m$^2$/g. A particularly preferred support is high purity $\alpha$-alumina having the above characteristics.

PREPARATION OF THE SUPPORTED SILVER CATALYST

In preparing the stable, supported silver catalyst of the instant invention, a suitable support is first contacted with the impregnating solution or mixtures thereof and subsequently heated at elevated temperatures to first evaporate the volatiles and finally to decompose the silver carboxylate/amine complex and activate the catalyst material. Although the preparation of the supported catalyst can be accomplished in two steps; i.e., an immersion step and an evaporation, activating, and decomposition step at incrementally increasingly elevated temperatures, it is preferable to prepare the catalyst of the instant invention in three distinct steps.

After the impregnating solution has been prepared, as described hereinabove, the substrate to be impregnated is contacted with the solution in a first step. This is preferably accomplished by immersion of the substrate in a suitably large body of impregnating solution to completely cover the substrate. The immersed substrate is then subjected to an evacuated atmosphere for a time period sufficient to remove entrapped air from the support pores at temperatures of from about 0° C to about 50° C and more preferably from about 20° C to about 40° C.

The impregnation time will depend on the characteristics of the substrate and the viscosity of the impregnating solution and can be readily determined by the skilled artisan. Although somewhat empirical, it is generally sufficient to contact the porous substrate with the impregnating solution for a time from about five minutes to several hours. When utilizing impregnating solutions of silver salts of polyalkylene polyamines, a time from about ten minutes to two hours is sufficient. After the substrate has been contacted for sufficient time, the vacuum is broken and excess solution physically drained from the substrate.

In a second step the drained substrate is dried in the presence of heated flowing air, or a heated flowing inert atmosphere, at temperatures from about 50° C to 150° C for a period sufficient to evaporate the volatiles. Generally the time required to dry the impregnated substrate is somewhat empirical and can be readily determined by the skilled artisan for a particular substrate and impregnating solution. Time periods of from about one to about twelve hours have been found sufficient. It should be noted that during the drying step temperatures in excess of about 150° C should be avoided as the complex may tend to decompose and/or cause the volatiles to evaporate so readily as to disturb the uniformity of the catalyst material. Although not required, it is found that first thoroughly drying the impregnated substrate prior to thermal decomposition yields a more uniform catalyst.

In the third step the dried impregnated substrate is heated in the presence of flowing air, or a flowing inert atmosphere to temperatures in excess of about 180° C and preferably from about 200° C to about 300° C to decompose the complexing agent and activate the supported silver catalyst materials. The time required to thoroughly decompose the silver salt/amine complex and activate the catalyst is somewhat empirical but generally times in the range from about one to twelve hours have been found sufficient.

It will be realized by the skilled artisan that when other solubilizing agents such as water, aqueous ammonia, aqueous alkyl amines, and the like are present in the complexing agent in accordance with the instant invention that the times required for drying may be somewhat lengthened. The specific times required are generally within the above broad limits and can be determined by the skilled artisan without undue experimentation. Additionally, when higher molecular weight amines are utilized, washing of the dried substrate may be advantageous to remove organic material prior to activation. The washing may be accomplished in a conventional manner with lower alkanols or other suitable solvents.

The catalysts thus prepared are surprisingly stable, physically strong and resistant to attrition. The stable silver supported catalyst are useful in the oxidation of ethylene to ethylene oxide in a manner well known to those skilled in the art such as the processes described in U.S. Pat. No. 3,119,837, British Pat. No. 1,314,613 and British Pat. No. 1,132,095. Additionally, the instant supported catalyst shows surprisingly high activity including high selectivity to oxide and high ethylene conversion rate in so-called "air" ethylene epoxidation processes.

The instant invention will be further illustrated by the following specific examples, which are given by way of illustration and not as limitations on the scope of this invention.

EXAMPLE I

This example illustrates preparation of the stable supported silver catalyst of the instant invention. In a first step, a silver oxalate was prepared. To an appropriate clean, dry vessel equipped with stirring apparatus were charged a solution of 18.4 g potassium oxalate dissolved in 150cc of deionized water and a solution of 34.0 g silver nitrate in 150cc deionized water. The two solutions were admixed at 60° C and atmospheric pressure by stirring for several minutes. The mixture was then filtered and the residue washed with four aliquots of hot, deionized water totaling 50cc. The residue was then further washed with two 25cc aliquots of absolute methanol. The residue was then air dried by evacuating the lower portion of the filter surface.

In a second step, the dried silver oxalate and 30 ml. of deionized water were added to a clean dry beaker and stirred until a slurry was obtained. To the stirred slurry was added 10cc of 30 wt. % NH$_4$OH and 25 g of diethylene triamine (DETA) yielding a dark, opaque homogeneous solution having a mole ratio of Ag/DETA of about 0.83.

In a third step the solution prepared in step two was used as an impregnating solution. The impregnating solution was drawn by suction into an evacuated clean dry 150 ml. stainless steel sampling cylinder containing 75 g of a commercial pure alumina support (3/6 inch spherical pellets) having a pore volume of .41 cc/g, a surface area of less than about 1 m$^2$/g and an average pore diameter of 5.9µ sold under the trade name LSA-005509 by the Norton Company. The vacuum was maintained at 40° C to 50° C for about 10 to 15 minutes until the pressure had dropped to about 10mm Hg. The vacuum was then released, and the container pressurized to 200 psig with nitrogen. After warming the cylinder to ambient temperature, the contents were allowed to stand under pressure for 30 minutes. The pressure was then released and excess solution drained.

In a fourth step the cylinder containing the wet impregnated material was attached to a forced-air heater, at approximately 130° C for 1 hour to dry the wet material. The dried material was then allowed to cool overnight.

In a fifth step the cylinder and contents were reheated to about 130° C, and then the temperature was raised to 250° C over a period of about 1 hour and held at that temperature for an additional hour. After cooling, the recovered material weighed 85 g and had a silvery-tan appearance. Upon inspection, the interior of the supported catalyst appeared somewhat non-uniform and the material was again heated at 250° C for an additional hour. After cooling, it was determined by analysis that the material contained 12.2 wt. % silver.

EXAMPLE II

This example illustrates the preparation of a supported catalyst using a silver oxalate/diethylenetriamine impregnating solution. Silver oxalate was initially prepared, as described in the first step of Example I and added to 30cc deionized water to form a stirred slurry. To the slurry was added a mixture of 30 g diethylenetriamine and 10cc deionized water, forming a dark, opaque impregnating solution. The prepared impregnating solution was used to immerse 50 g of the pure α alumina support material, as described in Example I (¼ inch spherical pellet). The support and covering solution was then placed under full pump vacuum. The vacuum was released to atmospheric pressure and the above sequence was once repeated. Upon draining, the wet impregnated support material was placed into a 150cc sampling cylinder, which was attached to a forced-air heater, and dried at a temperature of about 120° C for an hour. The sampling cylinder containing the dried material was then heated to about 250° C over a 30-minute period and held at that temperature for an hour. After cooling, the recovered impregnated material weighed 56 g and had a silvery-gray appearance. Analysis showed presence of 11.0 wt. % silver.

EXAMPLE III

This example illustrates catalysts prepared using impregnating solution of silver oxalate and bis(2-aminoethyl)ether (BAEE). Silver oxalate was prepared as described in the first step of Example I and added to 50cc deionized water containing 10cc of a 30% by weight NH$_4$OH solution to form a stirred slurry. To the slurry was slowly added 25 g of distilled BAEE. An additional 10cc of the NH$_4$OH (30% by weight) solution was added to dissolve the remaining undissolved materials. A dark homogeneous solution resulted.

Following the procedure in step 3 of Example I, the solution was drawn by suction into an evacuated 150cc stainless steel sampling cylinder containing 75 g of the catalyst material described in Example I. The support was impregnated and dried substantially as described in Example I except that the drying temperature was 120° C. The dried catalyst was then treated in accordance with the procedure of step 5, Example I to produce 80 g of a uniform gray-tan material which, upon analysis, was shown to contain 7.7% by weight silver.

EXAMPLE IV

This example illustrates preparation of a catalyst using a silver oxalate/polyoxyalkyleneamine complex impregnating solution. As in Example I, the silver oxalate was prepared and added to 30 g deionized water to form a stirred slurry. To the slurry was added 60 g of a polyoxypropylenediamine (mw 230) sold under the tradename JEFFAMINE ® D-230 by Jefferson Chemical Company, Inc. About 5cc of a 30% by weight aqueous NH$_4$OH solution was added to solubilize the remaining trace amount of solids. The solution was drawn by suction into a support material containing cylinder, as described in Example I. After impregnation, the remaining solution was drained. Drying was accomplished with forced air at temperatures of 120° C for three hours. Prior to decomposition, the dried material was washed with anhydrous methanol for five hours in an extraction thimble to extract undecomposed organic matter. Although this washing step is not necessary, it may be utilized to facilitate removal of high molecular weight organic matter which may form a residue during the decomposition step at higher temperatures. In this example, the methanol wet catalyst was returned to the sampling cylinder and again dried at 120° C for one hour prior to being heated at 250° C for an additional hour to effect decomposition and activation. Upon cooling, the recovered material weighed 80g, being slightly gray in color. Upon analysis, the material was shown to contain 9.0 wt. % silver.

EXAMPLE V

This example illustrates preparation of a catalyst from silver oxalate and imino bis(propylamine) impregnating solution. Silver oxalate was prepared, as described in Example I, and added to a beaker containing 30 g of deionized water. After a homogeneous slurry was formed, 10 ml of concentrated (30% by wt.) NH₄OH was added, followed by 30 g of imino bis(propylamine) (IBPA). The solution was used, as in Example I, to impregnate 50 g of the 3/16 inch spherical alumina support of Example I. When the solution was drained, it was observed that crystallization of the impregnating solution had occurred. The semi-solid was separated from the impregnated support with air. The contents of the cylinder were dried for about 17 hours with a forced-air heater at approximately 120° C. The dried material was then heated to about 250° C over a period of one hour. The temperature was maintained for an additional hour. After cooling, the finished catalyst had a silvery-gray color and was observed to have a fairly heavy silver coating on the external surface. The catalyst, upon analysis, was shown to contain 16.8 wt. % silver.

EXAMPLE VI

In this example, a prior art catalyst using silver oxalate, ethylenediamine and monoethanolamine was prepared in accordance with the procedure of Example I. Silver oxalate was prepared, as described in Example I, and added to a beaker containing 50cc deionized water. To the resulting slurry was added a mixture of 14 g ethylenediamine (EDA) and 14 g monoethanolamine (MEA). The resulting solution was drawn by suction into an evacuated 150cc stainless steel sampling cylinder containing 75 g of the 3/16 inch spherical support of Example I and the impregnation was carried out as therein described. The wet support was dried in a forced-air heater at approximately 130° C for two hours, and heated at approximately 250° C for 3 hours in dry air. The material was light tan color and contained 10 wt. % silver.

EXAMPLE VII

The seven catalysts described above in Examples I-VI were tested in a micro ethylene oxide reactor, a 0.2 inch interior diameter stainless steel tube, ten inches in length, operating at 200 psig and using 3.5 g of 30-40 mesh catalyst per test. The feed composition was approximately 7 wt. % ethylene, 6 wt. % oxygen, with the balance nitrogen and trace amounts of ethylene dichloride inhibitor. The reactor was operated at a temperature of 250° C and mass velocity of about 5 g of feed per gram of catalyst per hour. Enough moderator was added to give maximum selectivity at the chosen ethylene oxide production rate. Selectivities and conversions are given in mole percent. Results are given in Table I.

EXAMPLE VIII

Large scale preparation of catalyst using silver oxalate and DETA.

A large batch of fresh silver oxalate was prepared as follows: A 60° C solution containing 102 g of silver nitrate, A.R., and 500cc of deionized water was added slowly with stirring to an approximately 60° C solution of 44 g of ammonium oxalate slurry, A.R., in 500cc deionized water. The silver oxalate slurry was stirred for 20 minutes, then filtered through a Buchner funnel, washed with a 300cc deionized water in small portions and then with 300cc anhydrous methanol in small portions. The silver oxalate was dried under aspirator vacuum of 10 mm mercury and added slowly to a beaker containing 100cc deionized water to form an aqueous slurry. The slurry was chilled to below room temperature with an ice bath, while a solution containing 90 g DETA and 30 ml deionized water was added slowly, keeping the solution temperature below 60° C. The silver solution was removed from the ice bath after all the DETA solution had been added and was stirred until all solids had dissolved.

The impregnating solution thus formed was added in sufficient quantity to cover the surface of 326 g of the 3/16 inch spherical alumina support (Norton LSA-05509). The support and solution were placed under full pump vacuum, the vacuum released to atmospheric pressure and the immersed catalyst allowed to stand undisturbed for 30 minutes. The wet support was drained in a wire basked, then charged to a 50cc stainless steel sampling cylinder which was attached to a forced-air heater. The impregnated support was dried at approximately 125° C for one hour, then heated to 250° C over a period of one hour, and maintained at 250° C for one hour to complete the oxidation and decomposition process. After cooling, the catalyst was a uniform gray color inside and outside, weighed 359 g, and contained 9.7 wt. % silver.

The catalyst thus was tested in a pilot plant reactor operated at 245° C with a total feed rate of about 896 liters/hour. As before, the feed gas consisted of 7% ethylene, 7% oxygen, but now was 7.5 to 8% carbon dioxide, with a balance nitrogen with traces of inhibitor to improve selectivity.

This run resulted in a conversion of ethylene of 25%, a selectivity to ethylene oxide of 75% and 1.23 mole % ethylene oxide is the effluent. The productivity of the catalyst of the invention was 0.127 g ethylene oxide per gram of catalyst per hour. This compares to a productivity of a maximum of 0.0977 being the best productivity by commercially available ethylene oxide catalyst under substantially identical conditions, yielding an

TABLE I

| | Catalyst prepared according to indicated Examples | | | | | |
|---|---|---|---|---|---|---|
| | I (12.2)[1] | II (11.0)[1] | III (7.7)[1] | IV (9.0)[1] | V (16.8)[1] | VI[2] (10.0)[1] |
| Selectivity to ethylene oxide | 73 | 70 | 72 | 71 | 73 | 70 |
| C₂H₄ conversion | 34 | 41 | 34 | 36 | 32 | 35 |
| Normalized selectivity at constant conversion of 32% | 73 | 72 | 72 | 72 | 73 | 70 |
| Reactor temperature | 250° C | 250° C | 250° C | 250° C | 230° C | 250° C |

[1] Wt. % Ag by analysis
[2] Prior art catalyst using solubilizing/reducing impregnating solution in accordance with the procedures of the instant invention increase in productivity of about 30%. Even greater improvement was made over other commercially available catalysts in analogous runs.

EXAMPLE IX

The following example demonstrates the superior complexing characteristics of the amine containing complexing agents of the instant invention. Four separate impregnating solutions were prepared substantially as in Example I, keeping the solution at a temperature below 50° C. Silver oxalate was used as the silver salt. The formed solutions and their respective characteristics are listed in Table II.

TABLE II

| | COMPLEXING AGENT | | | |
|---|---|---|---|---|
| | Morpholine (50 ml) | Piperidine (50 ml) | N-ethyl-morpholine (50 ml) | Tetrahydrofurfuryl amine (50 ml) |
| initial solubility of silver oxalate[1] | homogeneous, stable | silver plated | None, two phase[3] | homogeneous stable |
| precipitate on standing | trace, finely divided black precipitate | large amount of crystalline material | N/A | Trace, finely divided precipitate |
| catalyst impregnation | no difficulty | N/A[2] | N/A[2] | No difficulty |

[1]Silver oxalate slurried in 30 ml water
[2]No catalyst preparation - solution unsatisfactory for attempt.
[3]A second aliquot of 50 ml N-ethyl morpholine was added with no change.

While the invention has been explained in relation to its preferred embodiment, it is to be understood that various modifications thereof will become apparent to those skilled in the art upon reading the specification and is intended to cover such modifications as fall within the scope of the appended claims.

What is claimed is:

1. A process for preparing a supported silver containing catalyst for the vapor phase epoxidation of ethylene with an oxygen containing epoxidizing agent comprising the steps of:
   contacting a porous, inorganic, catalyst support material with an impregnating solution comprising a silver carboxylate amine complex; and,
   heating the impregnated support material at temperatures from about 50° C to 300° C to evaporate volatiles, decompose said complex and activate sand catalyst,
   wherein said silver carboxylate/amine complex comprises a silver carboxylate dissolved in a solubilizing amount of an amine-containing complexing agent selected from the group consisting of
   (A) aliphatic polyamines containing at least three amino moieties wherein at least one is primary or secondary; and
   (B) aliphatic amino ethers containing at least one ether linkage and at least one amino moiety which is primary or secondary.

2. The process of claim 1 wherein said silver carboxylate amine complex is prepared by dissolving the silver carboxylate in a solubilizing amount of said amine complexing agent at temperatures of from 0° C to 50° C.

3. The process of claim 1 wherein said contacting is accomplished by:
   immersing said support material in said impregnating solution at temperatures of about 0° C to 50° C and atmospheric pressure; and
   evacuating the immersed support material at pressures of from about 1 to about 2 mm/Hg and temperatures of 20° C to 40° C to remove entrapped air.

4. The process of claim 3 wherein said silver carboxylate is silver oxalate and wherein said complexing agent is diethylenetriamine.

5. The process of claim 3 wherein said silver carboxylate is silver oxalate; and wherein said complexing agent is selected from a group consisting of morpholine, polyoxypropylenediamine having a molecular weight less than about 400 and tetrahydrofurfuryl amines.

6. The process of claim 3 wherein said support material is a high purity α-alumina material having an average pore diameter of from about 4 to about 6μ with a pore volume of from about 0.3 to about 0.6 cc/g and a surface area less than about 1 m²/g.

7. The process of claim 1 wherein said impregnating solution further comprises water.

8. The process of claim 1 wherein said silver carboxylate is selected from silver salts of monocarboxylic acids, dicarboxylic acids and mixtures thereof wherein the organic moiety contains less than about 10 carbon atoms.

9. The process of claim 1 wherein the said amine complexing agent is an aliphatic polyamine containing at least three amino moieties wherein at least one is primary or secondary.

10. The process of claim 1 wherein the amine complexing agent is an aliphatic amino ether containing at least one amino moiety which is primary or secondary.

11. The process of claim 1 wherein the said amine complexing agent is a polyamine of the formula:

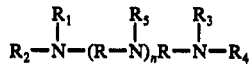

wherein R is a straight or branched chain alkylene radical having from 2 to about 4 carbon atoms, $R_1$, $R_2$, $R_3$, $R_4$ and $R_5$ are, independently, hydrogen or an alkyl radical of from 1 to 5 carbon atoms provided at least one of $R_1$, $R_2$, $R_3$, $R_4$ or $R_5$ is hydrogen; or $R_1$ and $R_2$, or $R_3$ and $R_4$ with the nitrogen to which they are attached form a piperazine ring and n is an integer of from 1 to about 4.

12. The process of claim 1 wherein the said amine complexing agent is an amino ether selected from a group consisting of morpholine, C-alkyl substituted morpholines wherein the alkyl radical contains from about 1 to 4 carbon atoms; furfuran amines and polyoxyalkylene amines having a molecular weight of less than about 1,000.

13. The process of claim 1 wherein the said amine complexing agent is diethylenetriamine.

14. The process of claim 1 wherein the said amine complexing agent is triethylenetetramine.

15. The process of claim 1 wherein the said amine complexing agent is morpholine.

16. The process of claim 1 wherein the said amine complexing agent is polyoxypropylenediamine having a molecular weight of about 230.

17. The process of claim 1 wherein the said amine complexing agent is polyoxypropylenediamine having a molecular weight less than about 400.

18. The process of claim 1 wherein the said silver carboxylate is silver oxalate.

19. The process of claim 1 wherein said silver carboxylate is silver oxalate and wherein said complexing agent is diethylenetriamine.

20. The process of claim 1 wherein said silver carboxylate is silver oxalate and said complexing agent is selected from the group consisting of C-alkyl substituted piperazine, and N-alkyl substituted piperazines.

21. The process of claim 1 wherein said silver carboxylate is silver oxalate; and wherein said complexing agent is selected from a group consisting of morpholine, polyoxypropylenediamine having a molecular weight of about 230, polyoxypropylenediamine having a molecular weight less than about 400 and tetrahydrofurfuryl amines.

22. The process of claim 1 wherein said support material is a high purity α-alumina material having an average pore diameter of from about 4 to about 6μ with a pore volume of from about 0.3 to about 0.6 cc/g and a surface area less than about 1 m$^2$/g.

* * * * *